US008067361B2

(12) United States Patent
Hill et al.

(10) Patent No.: US 8,067,361 B2
(45) Date of Patent: *Nov. 29, 2011

(54) CHAPERONIN 10 IMMUNOSUPPRESSION

(75) Inventors: Geoffrey R. Hill, Queensland (AU);
Tatjana Banovic, Queensland (AU);
Halle Morton, Coorparoo (AU); Alice Christina Cavanagh, Mitchelton (AU)

(73) Assignee: CBIO Limited, Eight Mile Plains, Queensland (AU)

( * ) Notice: Subject to any disclaimer, the term of this patent is extended or adjusted under 35 U.S.C. 154(b) by 0 days.

This patent is subject to a terminal disclaimer.

(21) Appl. No.: 12/572,195

(22) Filed: Oct. 1, 2009

(65) Prior Publication Data
US 2010/0099605 A1 Apr. 22, 2010

Related U.S. Application Data

(62) Division of application No. 10/534,193, filed as application No. PCT/AU2003/001467 on Nov. 6, 2003, now Pat. No. 7,618,935.

(30) Foreign Application Priority Data

Nov. 6, 2002 (AU) ............................... 2002952492

(51) Int. Cl.
C07K 14/00 (2006.01)
C07K 14/47 (2006.01)
A61K 38/16 (2006.01)
A61K 36/17 (2006.01)

(52) U.S. Cl. ........ 514/1.1; 514/885; 514/20.5; 530/350; 530/380

(58) Field of Classification Search .................. None
See application file for complete search history.

(56) References Cited

U.S. PATENT DOCUMENTS

| 5,989,804 | A | 11/1999 | Androphy et al. |
| 6,117,421 | A | 9/2000 | Morton et al. |
| 6,417,334 | B1 | 7/2002 | Morton et al. |

FOREIGN PATENT DOCUMENTS

| WO | WO 95/15338 | 6/1995 |
| WO | WO 01/17554 | 3/2001 |
| WO | WO 02/40038 | 5/2002 |

OTHER PUBLICATIONS

Chen et al., "Isolation, sequence analysis and characterization of a cDNA encoding human chaperonin 10" Biochim. Biophys. Acta, 1219, 189-190 (1994).
Cooke et al., "LPS antagonism reduces graft-versus host disease and preserves graft-versus-leukemia activity after experimental bone marrow transplantation." J. Clin. Invest., 107, 1581-1589 (2001).
Cooke et al, "Hyporesponsiveness of Donor Cells to Lipopolysaccharide Stimulation Reduces the Severity of Experimental Idoiopathic Pneumonia Syndrome: Potential Role for a Gut-Lung Axis of Inflammation." J. Immunol., 165, 6612-6619, (2000).
Cooke et al, "An Experimental Model of Idiopathic Pneumonia Syndrome After Bone Marrow Transplantaion: I. The Roles of Minor H Antigens and Endotoxin." Blood, 88, 3230-3239 (1996).
Dickson et al., "Cloning, Expression, and Purification of a Functional Nonacetylated Mammalian Mitochondrial Chaperonin 10." J. Biol. Chem., 269, 26858-864, (1994).
Ellis et al., "Molecular Chaperones." Annu. Rev. Biochem. 60, 321-47, (1991).
Hartman et al., "Identification of a mammalian 10-kDa heat shock protein, a mitochondrial chaperonin 10 homologue essential for assisted folding of trimeric ornithine transcarbamoylase in vitro." Proc. Natl. Acad. Sci. USA, 89, 3394-8, (1992).
Hill et al., "Interleukin-11 Promotes T Cell Polarization and Prevents Acute Graft-Versus-Host Disease after Allogeneic Bone Marrow Transplantation." J. Clin. Invest., 102, 115-123 (1998).
Hill et al., "Total Body Irradiation and Acute Graft-Versus-Host disease: The role of Gastrointestinal Damage and Inflammatory Cytokines." Blood, 90, 3204-3213, (1997).
Hill et al, "Differential roles of IL-1 and TNF-α on graft-versus-host disease and graft versus leukemia." J. Clin. Invest., 104, 459-467, (1999).
Kimura et al., The Journal of Int. Med. Res., 29:214-221, 2001.
Krijanovski et al, "Keratinocyte Growth Factor Separates Graft-Versus-Leukemia Effects From Graft-Versus-Host Disease." Blood, 94, 825-831, (1999).
Morton et al., "Immunosuppression detected in pregnant mice by rosette inhibition test." Nature, 249; 459-460, (1974).
Morton et al., "Studies of the Rosette Inhibition Test in Pregnant Mice: Evidence of Immunosuppression?" Proc. R. Soc. Land., 193; 413-9, (1976).
Morton et al., "Recent Advances in Mammalian Development." Current Topics in Developmental Biology, 23; 73-92 (1987).
Morton H., "Early pregnancy factor: An extracellular chaperonin 10 homologue." Immunol. Cell Biol., 76, 483-496, (1998).
Morton et al., Production of a recombinant form of early pregnancy factor that can prolong allogeneic skin graft survival time in rats. Immunology and Cell Biology, 78:6, p. 603-607, Dec. 2000. XP002463561.
Noonan et al., "Early pregnancy factor is immunosuppressive." Nature, 278, 649-51, (1979). Ogita et al., "Stress Responses in Graft and Native Intestine After Rat Heterotopic Small Bowel Transplantaion." Transplantation, 69, 2273-2277, (2000).
Rolfe et al., "Identification of two suppressor factors induced by early pregnancy factor." Clin. Exp. Immunol., 73, 2 19-225, (1988).
Ryan et al., "Isolation of a cDNA clone specifying rat chaperonin 10, a stress-inducible mitochondrial matrix protein synthesised without a cleavable presequence." FEBS Lett., 337, 152-156 (1994).
Speiser et al., "TNF Receptor p55 Controls Early Acute Graft-Versus-Host Disease." J. Immunol., 158, 5185-5190, (1997).
Somodevilla-Torres et al., Prot. Exp. And Purif., 32:276-287, 2003 (available online Oct. 2003).

*Primary Examiner* — Ronald Schwadron
(74) *Attorney, Agent, or Firm* — Foley & Lardner LLP; Stephen E. Reiter

(57) ABSTRACT

The invention is directed to the use of cpn10 in transplantation and particularly to treatment and/or prevention of graft versus host disease. The invention provides a method of administration of cpn10 to a donor and/or recipient animal or cells, tissues or organs derived from the donor, although in a particularly advantageous form treatment of both the donor and recipient animal. The method may further include the administration to the donor and/or recipient animal at least one other immunosuppressive agent to prevent or alleviate graft versus host disease.

6 Claims, 4 Drawing Sheets

AAGQAFRKFLPLFDRVLVERSAAETVTKGGIMLPEKSQGKVLQATVVA
VGSGSKGKGGEIQPVSVKVGDKVLLPEYGGTKVVLDDKDYFLFRDGDIL
GKYVD

*FIG. 1*

CHAPERONIN 10 IMMUNOSUPPRESSION

RELATED APPLICATION

This application is a divisional application of U.S. patent application Ser. No. 10/534,193, filed Dec. 7, 2005, now U.S. Pat. No. 7,618,935 which is a 371 of PCT/AU2003/001467, filed Nov. 6, 2003, which claims priority to Australian Application No. 2002952492, filed Nov. 6, 2002, which are hereby incorporated by reference in their entirety for all purposes.

FIELD OF INVENTION

THIS INVENTION relates to a method of treating graft versus host disease and other transplant-related immunological reactions and diseases. More particularly, this invention relates to a method of prophylactic and therapeutic treatment of graft versus host disease using chaperonin 10.

BACKGROUND OF THE INVENTION

Graft versus host disease (GVHD) is a condition that can develop when immunologically-competent cells have been introduced into an individual, for example during bone marrow or stem cell transplantation. GVHD refers to the immunological process whereby the newly transplanted cells mount a rejection response against host tissue. GVHD can develop after the transplantation or transfusion of bone marrow tissue, haematopoietic stem cells, unirradiated blood products and solid organs containing lymphoid tissue.

There are two types of GVHD, acute and chronic. Acute GVHD develops within the first three months following transplantation and clinical symptoms include dermatitis, enteritis and hepatitis. Chronic GVHD usually develops three months after transplantation and is an autoimmune syndrome affecting multiple organs and tissues, such as the skin, GI tract and liver.

Donor T cells are responsible for triggering the development of GVHD. Donor T cells recognise the host cell antigens as foreign and respond by proliferating and releasing cytokines which in turn may activate cells of the innate immune system.

Allogeneic bone marrow transplantation or haematopoietic cell transplantation remains the most effective curative therapy for the treatment of hematological malignancies, such as leukaemia, myeloma, lymphoma and aplastic anaemia. Severe acute GVHD is the primary cause of mortality and morbidity during bone marrow transplantation. Chronic GVHD can also result in death and survivors are often severely disabled.

Immunosuppressive drugs play a large part in the prevention, therapeutic treatment and management of acute and chronic GVHD. The drugs may be administered to the patient before and after the transplant. Current drugs used in the therapeutic treatment of GVHD include cyclosporine, methotrexate, tacrolimus, sacrolimus, mycophenolate mofetil and steroids. Immunosuppression regimens often involve the administration of a combination of drugs for maximal effect.

Chaperonin 10 (cpn10) is present in a variety of organisms, from bacteria to humans, and is a member of the heat shock family of proteins (chaperones) which are among the most evolutionary stable proteins in existence. The chaperone molecules are involved in post-translational folding, targeting and assembly of other proteins (Hartman et al., 1992, Proc. Natl. Acad. Sci. USA, 89, 3394-8) but do not themselves form part of the final assembled structure (Ellis et al., 1991, Annu. Rev. Biochem. 60, 321-47). These proteins play essential roles in normal cells but their production is upregulated during cellular stress (eg. metabolic disruption, infection, inflammation, transformation).

It was unexpectedly discovered that chaperonin 10 has the same amino acid sequence as Early Pregnancy Factor (EPF) (Morton et al., International Publication WO 95/15338). EPF is a pregnancy-associated substance that appears in the maternal serum within 6-24 hr of fertilization (Morton et al., 1974, Nature, 249; 459-460 and Morton et al., 1976, Proc. R. Soc. Lond., 193; 413-9). It is present for at least the first half of pregnancy and is essential for continued embryonic growth and survival (Morton et al., 1987, Current Topics in Developmental Biology 23; 73-92). It is now clear that EPF has many physiological functions and its production is not confined to pregnancy.

It has been reported that EPF can act as an immunosuppressant, release suppressor factors from lymphocytes (Rolfe et al., 1988, Clin. Exp. Immunol. 73, 219-225) and augment the rosette-inhibiting properties of an immunosuppressive anti-lymphocyte serum (Morton et al., 1974 and 1976, supra). EPF can suppress the delayed-type hypersensitivity reaction to trinitrochlorobenzene in mice (Noonan et al., 1979, Nature, 278, 649-51), suppress mitogen-induced lymphocyte proliferation (Athanasas-Platsis, 1993, PhD Thesis, The University of Queensland) and suppress IFN-$\gamma$ production by CD4+ T cells.

However, there has been no direct evidence as to whether EPF or cpn10 may have potential as an immunosuppressive agent in transplantation, and in particular in the prevention of GVHD. Chaperonin 60, a related heat shock protein, which can also act as an immunosuppressant, has not been shown to possess any therapeutic effects in GVHD. In fact, the prior art teaches that heat shock proteins may have adverse effects on transplantation (Ogita et al., 2000, Transplantation, 69, 2273-2277).

OBJECT OF THE INVENTION

The present inventors have realized the immunosuppressive drugs currently used for the therapeutic treatment and management of GVHD have the following significant shortcomings:
   (i) they induce severe side effects, for example, hypertension which may require additional medication for control, nephrotoxicity which occurs in up to 40% of patients and frequently forces the doctor to administer sub-optimal doses of the drug to limit the toxicity, CNS effects such as tremor, headache, depression, paraesthesia, blurred vision and seizures, increased risk of bacterial, fungal or viral infections, increased risk of cancer, particularly skin cancer, loss of appetite, nausea and increased hair growth;
   (ii) GVHD is resistant to the drugs in a significant percentage of patients and combination drug therapy is required;
   (iii) the drugs are very expensive; and
   (iv) the drugs have demonstrated adverse interactions with other therapeutic drugs, such as antibiotics, NSAIDs, anti-epileptics, and antifungals, immunizations, such as rubella and polio, and natural food, such as grapefruit (in the case of cyclosporin).

Therefore there is an enormous demand for the development of a new drug to treat and manage GVHD that has fewer side effects side effects than the treatments currently available and is more efficacious in patients that show a resistance to the current drugs on the market.

The present inventors have unexpectedly discovered that cpn10 possesses enormous clinical potential as a new therapy in the treatment and management of GVHD.

SUMMARY OF INVENTION

The invention is broadly directed to the use of cpn10 in transplantation and particularly to treatment and/or prevention of graft versus host disease.

The invention in a broad form provides administration of cpn10 to a donor and/or recipient animal or cells, tissues or organs derived from the donor, although in a particularly advantageous form the invention provides treatment of both the donor and recipient animal.

Therefore in a first aspect, the invention provides a method of therapeutically or prophylactically treating graft versus host disease (GVHD), including the steps of:

(i) administering a pharmaceutically-effective amount of chaperonin 10 (cpn10) or a derivative of cpn10 to a donor animal or cell, organ or tissue obtained therefrom; and (ii) administering to a recipient animal a pharmaceutically-effective amount of cpn10 or a derivative of cpn10, to thereby delay, ameliorate, suppress or otherwise reduce one or more symptoms of GVHD following transplantation of the one or more cells, tissues or organs to the recipient animal.

Preferably, the pharmaceutically-effective amount of cpn10 or a derivative of cpn10 is administered to a recipient animal both before and after step (ii).

Preferably, the pharmaceutically-effective amount of cpn10 or derivative of cpn10 administered to an animal is within the range 0.1-100 mg per kg/body weight. More preferably, it is within the range 0.1-10 mg per kg/body weight.

Preferably, the animal is a mammal.

Preferably, the mammal is a human.

Suitably, the cell, tissue or organ is bone marrow or is derived from bone marrow.

Suitably, the method of therapeutically or prophylactically treating GVHD further includes the step of administering to said donor animal and/or said recipient animal at least one other immunosuppressive agent selected from the group consisting of cyclosporin, tacrolimus, sirolimus, mycophenolate mofetil and methotrexate.

Suitably, the method of therapeutically or prophylactically treating GVHD further includes the step of administering to said donor animal and/or said recipient animal a steroid.

In a second aspect, there is provided a method of inhibiting, suppressing or otherwise reducing TNFα production in an animal including the step of administering to said animal a pharmaceutically-effective amount of cpn10 or derivative of cpn10 to thereby, inhibit, suppress or otherwise reduce production of TNFα in said animal.

Preferably, the animal is a mammal.

Preferably, the mammal is a human.

According to this aspect, the invention also provides a method of inhibiting, suppressing or otherwise reducing TNFα production by one or more cells, tissues or organs obtained from an animal including the step of administering to said cells, tissues or organs a pharmaceutically-effective amount of cpn10 or derivative of cpn10 to thereby inhibit production of TNFα by said animal.

In a third aspect, the invention provides a method of inducing, augmenting or otherwise increasing IL-10 production in an animal including the step of administering to said animal a pharmaceutically-effective amount of cpn10 or derivative of cpn10 to thereby induce, augment or otherwise increase production of IL-10 in said animal.

Preferably, the animal is a mammal.

Preferably, the mammal is a human.

According to this aspect, the invention also provides a method of inducing, augmenting or otherwise increasing TNFα production by one or more cells, tissues or organs obtained from an animal including the step of administering to said cells, tissues or organs a pharmaceutically-effective amount of cpn10 or derivative of cpn10 to thereby induce production of IL-10 by said animal.

In a fourth aspect, there is provided a pharmaceutical composition for use according to the method of any of the aforementioned aspects comprising a pharmaceutically-effective amount of cpn10 or a derivative of cpn10, and a pharmaceutically-acceptable carrier, excipient or diluent.

Preferably, the at least one other immunosuppressive agent is an immunosuppressive drug or a specific antibody directed against B or T lymphocytes or surface receptors that mediate their activation.

Preferably, the immunosuppressive drug is any one of cyclosporin, tacrolimus, sirolimus, mycophenolate mofetil and methotrexate.

In a fifth aspect, there is provided a pharmaceutical composition of the fourth aspect further comprising a steroid.

Preferably, said cpn10 protein has an amino acid sequence set forth in FIG. 1 (SEQ ID NO: 1).

Throughout this specification, "comprise", "comprises" and "comprising" are used inclusively rather than exclusively, will be understood to imply the inclusion of a stated integer or group of integers but not the exclusion of any other integer or group of integers.

BRIEF DESCRIPTION OF THE FIGURES

FIG. 1: The amino acid sequence of the cpn10 protein (SEQ ID NO:1).

DETAILED DESCRIPTION OF INVENTION

Figure 2:
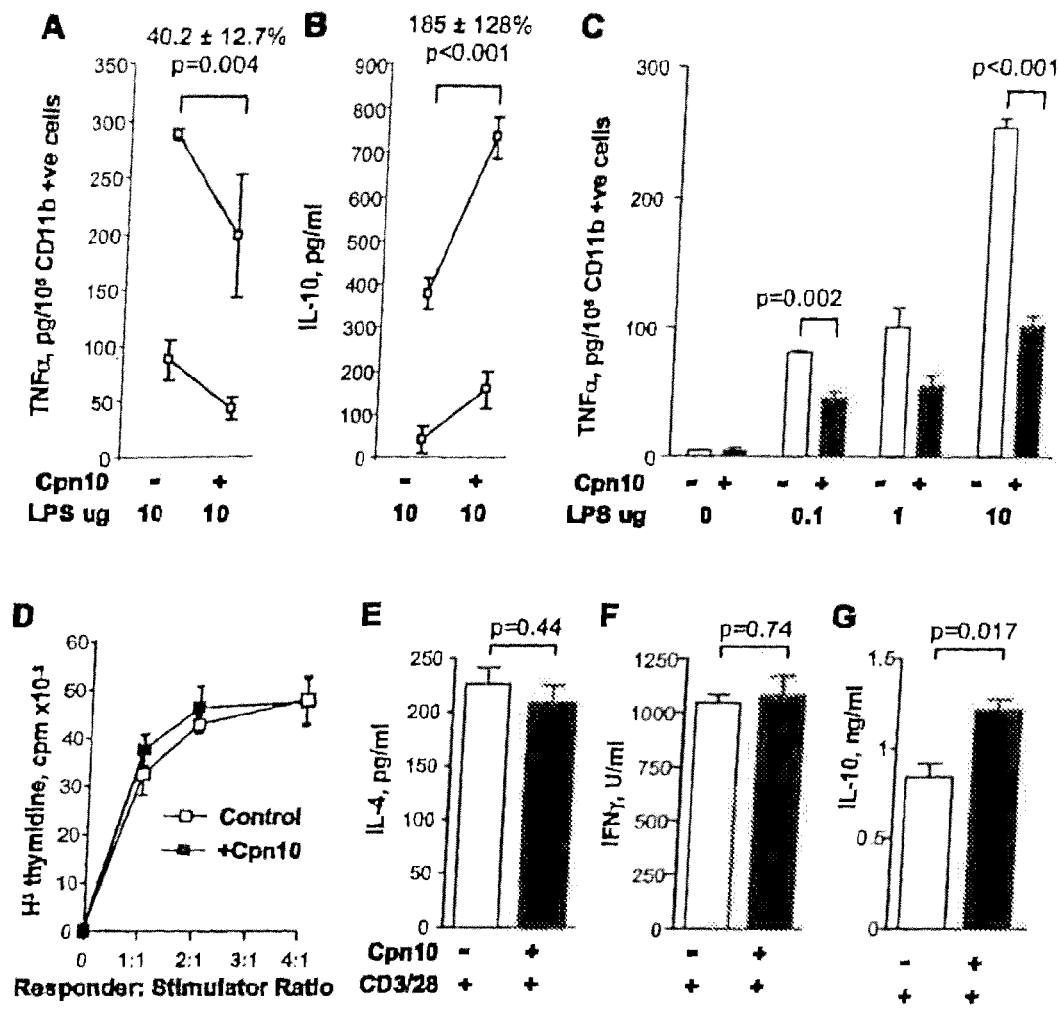
FIG. 2A-G: The effect of in vivo cpn10 treatment on LPS- and alloantigen-induced proinflammatory responses of mice peritoneal macrophages and on T cell differentiation.

The inventors have demonstrated that cpn10 has significant immunosuppressive activity in an in vivo mouse transplantation model and that cpn10 treatment increases the survival rate of mice suffering from GVHD. This is the first demonstration of the beneficial immunosuppressive effects of cpn10 and increased survival rates in an in vivo GVHD model.

The effectiveness of the cpn10 treatment is increased if both donor and recipient animals are treated with cpn10 prior to the transplant procedure. The invention also demonstrates that cpn10 inhibits lipopolysaccharide-mediated TNFα secretion and promotes IL-10 production in mouse macrophages. IL-10 is a potent immunosuppressive cytokine that is a powerful inhibitor of adaptive and innate immune responses to LPS.

Acute GVHD following allogeneic bone marrow transplantation (BMT) is a T cell mediated disease in which donor T cells recognise disparate host antigens and differentiate in a Th1 dominant fashion. The resulting T cell derived Th1 cytokines prime donor mononuclear cells that release cytopathic quantities of inflammatory cytokines (e.g. TNFα) when they come into contact with lipopolysaccharide (LPS). LPS leaks through the gastrointestinal mucosa which is damaged by GVHD and by the preceding radiation. Therefore TNFα, together with the dysregulated cytotoxic cytokine production induces apoptosis in host tissue. GVHD mortality in BMT models is prevented by T cell directed immunosuppression, particularly by agents that inhibit IL-2 generation.

The present invention is exemplified in respect of bone marrow transplantation. However, it will be appreciated the concept is applicable to other cells, tissues and organs that include immuno-competent cells capable of initiating an immune response in the host. Non-limiting examples of such cells, tissues and organs include liver, lung, heart, kidney and stem and progenitor cells.

The invention as described herein may be broadly applicable to any animal but is particularly directed to mammals, and preferably humans. For example, the invention may be directed to a transplantation in livestock, domestic animals, laboratory animals and performance animals (for example, racehorses and camels).

For the purposes of this invention, by "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material may be in native, chemical synthetic or recombinant form.

By "protein" is meant an amino acid polymer. The amino acids may be natural or non-natural amino acids D- and L-amino acids, as are well understood in the art.

A "peptide" is a protein having no more than fifty (50) amino acids.

A "polypeptide" is a protein having more than fifty (50) amino acids.

The term "nucleic acid" as used herein designates single- or double stranded mRNA, RNA, cRNA, RNAi and DNA inclusive of cDNA and genomic DNA.

By "immunosuppressive agent" is meant an agent that can prophylactically or therapeutically suppress an autoimmune or immune response against a transplanted allogeneic or xenogeneic cell, tissue or organ, or to suppress graft versus host disease.

Preferably, the pharmaceutically effective amount of cpn10 administered to an individual is within the range 0.1-100 mg.

More preferably, the pharmaceutically-effective amount of cpn10 administered to an individual is within the range 0.1-10 mg.

It will be appreciated by the skilled person that the aforementioned pharmaceutically-effective amounts are calculated in terms of a typical 70 kg human. Accordingly, doses may vary depending on the weight, age, sex, general health and fitness of the individual and any other treatments to which the individual is being subjected. Furthermore, the amount of cpn10 administered will be interdependent with the frequency and timing of administration.

It will also be appreciated that the aforementioned pharmaceutically-effective amounts of cpn10 can be administered to animals, for example, domestic animals and livestock. Doses would vary depending on the weight and type of animal, as would be apparent to those of skill in the art.

The cpn10 administered to a human or other animal may be any form of isolated cpn10, including but not limited to recombinant cpn10 (SEQ ID NO: 1), native cpn10, pegylated cpn10, recombinant cpn10-GSM or any other derivative protein of cpn10.

Suitable cpn10 nucleotide and amino acid sequences are well known in the art, although for convenience the skilled person is referred to the following mammalian cpn10 sequences:

(i) human cpn10 (NCBI Entrez Accession No. U07550; Chen et al., 1994, Biochim. Biophys. Acta. 1219, 189-190)

(ii) mouse cpn10 (NCBI Entrez Accession No. U09659; Dickson et al., 1994, J. Biol. Chem., 269, 26858-864); and (iii) rat cpn10 (NCBI Entrez Accession No. X71429; Ryan et al., 1994, FEBS Lett., 337, 152-156).

Both donor and recipient can be treated with cpn10 prior to the transplant procedure.

Preferably, the donor undergoes cpn10 treatment for no more than 7 days prior to the transplant procedure. More preferably, the donor undergoes cpn10 treatment for 2 to 5 days prior to the transplant procedure.

Preferably, the recipient undergoes cpn10 treatment for no more than 7 days prior to the transplant procedure and no more than 90 days after the procedure. More preferably, the recipient undergoes cpn10 treatment for 2 to 5 days prior to the transplant procedure and no more than 60 days after the procedure. Even more preferably, the recipient undergoes cpn10 treatment for 2 to 5 days prior to the transplant procedure and 10 to 30 days after the procedure.

As used herein, "derivative" proteins of the invention are proteins, such as cpn10 proteins, which have been altered, for example by conjugation or complexing with other chemical moieties or by post-translational modification techniques as would be understood in the art, inclusive of fusion partner proteins.

Other derivatives contemplated by the invention include, but are not limited to, pegylation, modification to side chains, incorporation of unnatural amino acids and/or their derivatives during peptide, polypeptide or protein synthesis and the use of crosslinkers and other methods which impose conformational constraints on the polypeptides, fragments and variants of the invention. Examples of side chain modifications contemplated by the present invention include modifications of amino groups such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with $NaBH_4$; reductive alkylation by reaction with an aldehyde followed by reduction with $NaBH_4$; and trinitrobenzylation of amino groups with 2, 4,6-trinitrobenzene sulphonic acid (TNBS).

The carboxyl group may be modified by carbodimide activation via O-acylisourea formation followed by subsequent derivitization, by way of example, to a corresponding amide.

The guanidine group of arginine residues may be modified by formation of heterocyclic condensation products with reagents such as 2,3-butanedione, phenylglyoxal and glyoxal.

Sulphydryl groups may be modified by methods such as performic acid oxidation to cysteic acid; formation of mercurial derivatives using 4-chloromercuriphenylsulphonic acid, 4-chloromercuribenzoate; 2-chloromercuri-4-nitrophenol, phenylmercury chloride, and other mercurials; formation of a mixed disulphides with other thiol compounds; reaction with maleimide, maleic anhydride or other substituted maleimide; carboxymethylation with iodoacetic acid or iodoacetamide; and carbamoylation with cyanate at alkaline pH.

Tryptophan residues may be modified, for example, by alkylation of the indole ring with 2-hydroxy-5-nitrobenzyl bromide or sulphonyl halides or by oxidation with N-bromosuccinimide.

Tyrosine residues may be modified by nitration with tetranitromethane to form a 3-nitrotyrosine derivative.

The imidazole ring of a histidine residue may be modified by N-carbethoxylation with diethylpyrocarbonate or by alkylation with iodoacetic acid derivatives.

Examples of incorporating unnatural amino acids and derivatives during peptide synthesis include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids.

Derivatives may also include fusion partners and epitope tags. Well known examples of fusion partners include, but are not limited to, glutathione-S-transferase (GST), Fe portion of human IgG, maltose binding protein (MBP) and hexahistidine ($HIS_6$) (SEQ ID NO: 2), which are particularly useful for isolation of the fusion protein by affinity chromatography. For the purposes of fusion polypeptide purification by affinity chromatography, relevant matrices for affinity chromatography are glutathione-, amylose-, and nickel- or cobalt-conjugated resins respectively. Many such matrices are available in "kit" form, such as the QIAexpress™ system (Qiagen) useful with ($HIS_6$) (SEQ ID NO: 2) fusion partners and the Pharmacia GST purification system.

One particular example of a fusion partner is GST, such as described in Ryan et al. (supra). In some cases, the fusion partners also have protease cleavage sites, such as for Factor $X_a$ or Thrombin, which allow the relevant protease to partially digest the fusion polypeptide of the invention and thereby liberate the recombinant polypeptide of the invention therefrom. The liberated polypeptide can then be isolated from the fusion partner by subsequent chromatographic separation. Upon cleavage of GST-cpn10 the derivative GSM-cpn10 protein is produced, for example.

Fusion partners according to the invention also include within their scope "epitope tags", which are usually short peptide sequences for which a specific antibody is available. Well known examples of epitope tags for which specific monoclonal antibodies are readily available include c-myc, haemagglutinin and FLAG tags.

Cpn10 proteins of the invention (inclusive of fragments, variants, derivatives and homologues) may be prepared by any suitable procedure known to those of skill in the art, including chemical synthesis and recombinant expression.

Preferably, cpn10 is recombinant cpn10.

For example, the recombinant cpn10 protein may be prepared by a procedure including the steps of:
  (i) preparing an expression construct which comprises an isolated nucleic acid encoding cpn10, operably-linked to one or more regulatory nucleotide sequences in an expression vector;
  (ii) transfecting or transforming a suitable host cell with the expression construct; and
  (iii) expressing the recombinant protein in said host cell.

An "expression vector" may be either a self-replicating extra-chromosomal vector such as a plasmid, or a vector that integrates into a host genome.

By "operably-linked" is meant that said regulatory nucleotide sequence(s) is/are positioned relative to the recombinant nucleic acid of the invention to initiate, regulate or otherwise control transcription.

Regulatory nucleotide sequences will generally be appropriate for the host cell used for expression. Numerous types of appropriate expression vectors and suitable regulatory sequences are known in the art for a variety of host cells.

Typically, said one or more regulatory nucleotide sequences may include, but are not limited to, promoter sequences, leader or signal sequences, ribosomal binding sites, transcriptional start and termination sequences, translational start and termination sequences, splice donor/acceptor sequences and enhancer or activator sequences.

Constitutive or inducible promoters as known in the art are contemplated by the invention and include, for example, tetracycline-repressible and metallothionin-inducible promoters. The promoters may be either naturally occurring promoters, or hybrid promoters that combine elements of more than one promoter.

In a preferred embodiment, the expression vector contains a selectable marker gene to allow the selection of transformed host cells. Selectable marker genes are well known in the art and will vary with the host cell used.

Suitable host cells for expression may be prokaryotic or eukaryotic, such as *Escherichia coli* (DH5α for example), yeast cells, SF9 cells utilized with a baculovirus expression system, CHO cells, COS, CV-1 and 293 cells, without limitation thereto.

The recombinant cpn10 protein may be conveniently prepared by a person skilled in the art using standard protocols as for example described in Sambrook et al., MOLECULAR CLONING. A Laboratory Manual (Cold Spring Harbor Press, 1989), incorporated herein by reference, in particular Sections 16 and 17; CURRENT PROTOCOLS IN MOLECULAR BIOLOGY Eds. Ausubel et al., (John Wiley & Sons, Inc. 1995-1999), incorporated herein by reference, in particular Chapters 10 and 16; and CURRENT PROTOCOLS IN PROTEIN SCIENCE Eds. Coligan et al., (John Wiley & Sons, Inc. 1995-1999) which is incorporated by reference herein, in particular Chapters 1, 5 and 6.

An example of production and purification of recombinant synthetic cpn10 using the pGEX system is provided in WO 95/15338. A high yielding bacterial expression system known to produce active cpn10 (Ryan et al., supra) was used to produce the cpn10 (SEQ ID NO: 1) used in the experiments described herein.

Pharmaceutical Compositions

The invention provides a use of cpn10 for the therapeutic treatment of diseases or medical conditions caused by cell, tissue or organ transplantation, in particular GVHD.

The invention also provides pharmaceutical compositions that comprise cpn10 or a derivative of cpn10.

Suitably, the pharmaceutical composition comprises an appropriate pharmaceutically-acceptable carrier, diluent or excipient.

Suitably, the pharmaceutical composition comprises cpn10 or a derivative of cpn10, a pharmaceutically-acceptable carrier, diluent or excipient and at least one other immunosuppressive agent. Preferably, the other immunosuppressive agent is an immunosuppressive drug or a specific antibody directed against B or T lymphocytes or surface receptors that mediate their activation. More preferably, the immunosuppressive agent is any one of cyclosporin, tacrolimus, sirolimus, mycophenolate mofetil and methotrexate. The pharmaceutical composition may also comprise a steroid.

By "pharmaceutically-acceptable carrier, diluent or excipient" is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates and pyrogen-free water.

A useful reference describing pharmaceutically acceptable carriers, diluents and excipients is Remington's Pharmaceutical Sciences (Mack Publishing Co. N.J. USA, 1991) which is incorporated herein by reference.

Any safe route of administration may be employed for providing a patient with the composition of the invention. For example, oral, rectal, parenteral, sublingual, buccal, intravenous, intra-articular, intra-muscular, intra-dermal, subcutaneous, inhalational, intraocular, intraperitoneal, intracerebroventricular, transdermal and the like may be employed. Intra-muscular and subcutaneous injection is appropriate, for example, for administration of immunogenic compositions, vaccines and DNA vaccines.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

The above compositions may be administered in a mariner compatible with the dosage formulation, and in such amount as is pharmaceutically-effective. The dose administered to a patient, in the context of the present invention, should be sufficient to affect a beneficial response in a patient over an appropriate period of time. The quantity of agent(s) to be administered may depend on the subject to be treated inclusive of the age, sex, weight and general health condition thereof, factors that will depend on the judgement of the practitioner.

So that the present invention may be more readily understood and put into practical effect, the skilled person is referred to the following non-limiting examples.

Examples

Methods

Transplantation

Mice were transplanted according to a standard protocol as described in Hill et al., 1997, Blood, 90, 3204-3213, and Hill et al., 1999, J. Clin. Invest., 104, 459-467. On day 0 B6D2F1 mice received 1400 cGy total body irradiation (TBI, $^{137}$Cs source) in two doses separated by three hours to minimize gastrointestinal toxicity. $5 \times 10^6$ bone marrow cells and $2 \times 10^6$ nylon wool purified splenic donor T cells from B6 mice (allogenic) or B6D2F1 mice (syngeneic) were resuspended in 0.25 ml of Leibovitz's L-15 media and injected intravenously into the irradiated recipients.

Preparation of Recombinant cpn10

XL1-Blue E. coli cells were transformed with cpn10 using the expression vector pPL550 and grown at 37° C. Cells in exponential growth were induced to express protein by temperature increase to 42° C. for 4 h. Cells were pelleted, resuspended in 30 ml 0.025 M TrisHCl pH 8.0 and stored at −30° C.

A cell pellet from a 1 L culture was thawed, cells were lysed with lysozyme (100 μg/ml; 15 min at 37° C.), followed by sonication (5×10 sec, 4° C.) and cellular debris was removed by centrifugation (30 min, 4° C., 48 384×g).

Cpn10 was purified from the clarified lysate by ion-exchange and hydrophobic interaction chromatography. The protein was identified in column fractions as an ~10 kDa band using SDS-PAGE on 10-20% Tris-Tricine gels (100×100×1 mm; Novex).

Lysate was applied to a 200 ml column of Macroprep HighQ (BIO-RAD) using 0.025 M TrisHCl pH 8.0 as running buffer at a flow rate of 8 ml/min. The unbound fraction was retained and pH adjusted to 6.8. The sample was applied to a 5 ml EconoPac S cartridge (BIO-RAD) using 0.025 M sodium phosphate buffer pH 6.8 as running butler at a flow rate of 2 ml/min. The column was eluted with a gradient of 0→1 M NaCl in 0.025 M sodium phosphate buffer pH 6.8, applied over 30 min at 2 ml/min.

Cpn10 containing fractions were pooled and an equal volume of 3 M $(NH_4)_2SO_4$ in 0.05 M sodium phosphate buffer pH 6.8 was added. The sample was applied to a 5 ml Econopac Methyl HIC cartridge using 1.5 M $(NH_4)_2SO_4$ in 0.05 M sodium phosphate buffer pH 6.8 as running buffer at a flow rate of 2 ml/min. The column was eluted with a gradient of 1.5-40 M $(NH_4)_2SO_4$ in 0.05 M sodium phosphate butler pH 6.8, applied over 15 min at 2 ml/min.

Cpn10 containing fractions were pooled, dialysed against saline overnight, dispensed in appropriate aliquots and stored at −30° C.

Cpn10 Treatment

Recombinant human cpn10 was diluted in PBS before injection. Mice were injected subcutaneously with cpn10 each day (10 μg/dose or 100 fig/dose) before or after BMT as described. Mice from the control groups received injection of diluent only.

Assessment of GVHD

The degree of systemic GVHD was assessed by survival and by a scoring system which sums changes in five clinical parameters: weight loss, posture (hunching), activity, fur texture and skin integrity (maximum index=10) (Cooke et al., 1996, Blood, 88, 3230-3239; Hill et al., 1999, J. Clin. Invest., 104, 459-467). Individual mice were ear-tagged and graded weekly from 0 to 2 for each criterion. Animals with severe clinical GVHD (scores>6) were sacrificed according to ethical guidelines and the day of death deemed to be the following day.

Statistical Analysis

Survival curves were plotted using Kaplan-Meier estimates and compared by log-rank analysis. The Mann Whitney-U Test was used for the statistical analysis of clinical scores. P<0.05 was considered statistically different.

Example 1

In Vitro Mouse Macrophage Experiments

In vitro experiments were carried out to determine the effect of cpn10 in a physiological cell population.

Mice

Female C57BL/6 (B6, $H-2^b$, $Ly-5.2^+$), B6 $Ptprc^a$ Ly-5a ($H-2^b$, $Ly-5.1^+$) and B6D2F1 ($H-2^{b/d}$, $Ly-5.2^+$) mice were purchased from the Australian Research Centre (Perth, Western Australia, Australia). C57BL/6 IL-10-4-mice (B6, $H-2^b$, $Ly-5.2^+$) were supplied by the Australian National University (Canberra, Australia). The age of mice used as transplant recipients ranged between 8 and 14 weeks. Mice were housed in sterilised micro-isolator cages and received acidified autoclaved water (pH 2.5) and normal chow for the first two weeks post-transplantation.

Bone Marrow Transplantation

Mice were transplanted according to a standard protocol (Hill et al., 1997 supra). Briefly, on day 1, B6D2F1 mice received 1300 cGy total body irradiation ($^{137}$Cs source at 108 cGy/min), split into two doses separated by 3 hours to minimise gastrointestinal toxicity. Donor bone marrow (5×106 per animal) and splenic T cells (3×10$^6$ per animal) were resuspended in 0.25 ml of Leibovitz's L-15 media (Gibco BRL, Gaithersburg Md.) and were injected intravenously into recipients. Survival was monitored daily, and the GVHD clinical scores were measured weekly. Cpn10 or control diluent was injected subcutaneously at doses of 100 ug per animal. The degree of systemic GVHD was assessed as described above.

Cell Cultures

The culture media used throughout was 10% FCS/IMDM (JRH Biosciences, Lenexa, Kans.) supplemented with 50 units/ml penicillin, 50 p g/ml streptomycin, 2 mM L-glutamine, 1 mM sodium pyruvate, 0.1 mM non-essential amino acid, 0.02 mM 13-mercaptoethanol, and 10 mM HEPES. Experiments were performed at pH 7.75 and 37° C. in a humidified incubator supplemented with 5% $CO_2$.

For in vitro LPS stimulation experiments, peritoneal macrophages or splenocytes were stimulated with graded concentrations of LPS, TNFα and IL-10 determined in culture supernatants at 5 hours and 48 hours respectively. For in vitro allo-antigen experiments, purified C57BL/6 T cells were cultured in 96 well plates (Becton Dickinson, Franklin Lakes, N.J.) with 105 irradiated (2000 cGy) B6D2F1 peritoneal macrophages (primary MLC) and supernatants harvested at 72 hours. Cultures were then pulsed with $^3$H-thymidine (1 μCi per well) and proliferation was determined 16 hrs later on a 1205 Betaplate reader (Wallac, Turku, Finland). For in vitro mitogen stimulation, purified C57BL/6 T cells were cultured in flat bottomed 96 well plates, pre-coated with monoclonal CD3 and CD28 at final concentrations of 10 μg/ml. Supernatants were harvested at 48 hours and cultures pulsed with $^3$-thymidine (1 μCi per well). Proliferation was determined 16 hrs later.

Cytokine ELISAS

The antibodies used in the IFNγ, IL-10, IL-4 and TNFα assays were purchased from PharMingen (San Diego, Calif.) and assays were performed according to the manufacturer's protocol. Briefly, samples were diluted 1:3 to 1:24 and cytokines were captured by the specific primary monoclonal antibody (mAb) and detected by biotin-labelled secondary mAbs. The biotin-labelled assays were developed with strepavidin and substrate (Kirkegaard and Perry laboratories, Gaithersburg, Md.). Plates were read at 450 nm using the Spectraflour Plus microplate reader (Tecan, Durham, N.C.). Recombinant cytokines (PharMingen) were used as standards for ELISA assays. Samples and standards were run in duplicate and the sensitivity of the assays were 0.063 U/ml for IFNγ, and 15 pg/nil for IL-10, IL-4 and TNFα.

Results

In vivo administration of cpn10 reduced the capacity of peritoneal macrophages to produce TNFα (FIG. 2A). B6 mice (n=3) were treated for 5 days with cpn10 (100 μg, once daily) (cpn10+) or control diluent (cpn10−). Peritoneal macrophages were harvested by peritoneal lavage on day 6 and pooled from individual animals within the treatment group. Cells were plated at 2×10$^5$/well in the absence (not shown) or presence of LPS (1 ug/ml). Culture supernatants were collected at 5 hours and levels of TNFα (pg/ml) were assessed by ELISA. Results are normalized to production per 10$^5$ macrophages based on CD11b staining. FIG. 2A shows data from two identical experiments. LPS-induced secretion of TNFα was reduced by 40% from these cells.

In vivo treatment with cpn10 augmented IL-10 production from splenocytes (FIG. 2B). B6 mice were treated with either cpn10 or control diluent as described above. Splenocytes were harvested on day 6 and pooled from individual animals within a treatment group before culture at 5×10$^5$/well in the absence (not shown) or presence of LPS (10 ug/ml). Culture supernatants were collected at 48 hours and levels of IL-10 (pg/ml) determined by ELISA. The data from two identical experiments is shown in FIG. 2B. Significantly increased IL-10 production was observed compared to control animals.

In vivo treatment with cpn10 reduced TNFα production from IL10$^{-/-}$ peritoneal macrophages (FIG. 2C). IL10$^{-/-}$ B6 mice were treated with cpn10 or control diluent and peritoneal macrophages were harvested by peritoneal lavage on day 6 and pooled from individual animals within the treatment group. Alter 5 hours of cultivation in the absence (LPS 0) or presence of LPS (0.1, 1 and 10 ug/ml), the amount of TNFα was determined in the culture supernatants. Cpn10-mediated reduction in LPS-induced TNFα production (FIG. 2A) does not require IL-10 since similar reductions in TNFα secretion were observed when peritoneal macrophages from cpn10 treated IL-10$^{-/-}$ mice were stimulated with LPS in vitro. Thus reduced TNFα secretion and increased IL-10 production appears to be independent consequences of cpn10 treatment.

Cpn10 treatment did not appear to affect T cell IFNγ or IL-4 secretion. Previous reports have suggested that cpn10 can inhibit T cell proliferation in response to mitogen (Morton H. 1998 *Immunol. Cell Biol.,* 76, 483-496). Th1 immune responses are usually characterised by proinflammatory cytokines such as TNFα and IFNγ. Th2 responses involve IL-4 and IL-10 secretion and regulatory T cell (Treg) responses are characterised by IL-10 and TGFβ production. Since Th2 and Treg responses suppress proliferation and Th1 responses suppress cytokine production, the ability of cpn10 to influence T cell differentiation was investigated.

In vivo administration of cpn10 did not affect proliferative response of T lymphocytes to alloantigen (FIG. 2D). B6 mice (n=3) were treated with daily injections of cpn10 or control diluent. The splenocyte-derived T cell populations were stimulated in vitro with allogenic splenocytes for 7 days in a mixed lymphocyte culture (MLC). Purified T cells ($0.5 \times 10^5$, $1 \times 10^5$ and $2 \times 10^5$/well) were stimulated with irradiated allogeneic B6D2F1 peritoneal macrophages ($0.5 \times 10^5$/well) and proliferation was measured at 72 hours via standard $^3$[H] Thymidine incorporation assay. The values plotted in FIG. 2D represent mean±SE of triplicate wells. The proliferation of T cells within these MLCs did not differ significantly between cpn10 treated and control animals indicating that cpn10 is not a T cell growth regulator.

FIGS. 2E-G show the effects of in vivo administration of cpn10 on T cell differentiation. B6 animals were treated in vivo with cpn10 as described above. T cells ($2 \times 10^6$/well) from cpn10 treated and vehicle treated animals were stimulated in culture for 7 days with irradiated allogeneic B6D2F1 splenocytes ($3 \times 10^6$/well) (primary mixed lymphocyte culture). On day 7 T cells were collected and re-stimulated with plate-bound antibodies to CD3 and CD28 which stimulate T cells. Culture supernatants were harvested at 24 hours and concentrations of IFNγ, IL4 and IL-10 were determined by ELISA. The concentration values in FIGS. 4E-G represent the mean±SE of triplicate wells.

Neither T cell IL-4 secretion (FIG. 2E) nor IFNγ secretion (FIG. 2F) differed significantly between cpn10 treated and control animals suggesting that cpn10 does not influence the Th1/Th2 balance.

In contrast, T cell IL-10 secretion was significantly elevated (FIG. 2G). A similar elevation in IL-10 secretion was also observed when cpn10 treatment was carried out in vitro during cell culture (MLC), rather than in vivo, and proliferation. IFNγ and IL-4 was again unaffected (data not shown). These data indicate that cpn10 can enhance IL-10 production in response to stimulation with LPS and alloantigen, and suggests that cpn10-enhanced IL-10 production may be due in part from T cell-derived IL-10.

Example 2

Effect of Pre- and Post-Transplant Treatment with cpn10 in the in Vivo GVDH Model In vivo experiments were conducted to investigate if the administration of cpn10 in the peri-transplant period could prevent GVHD.

Post-Treatment Administration of cpn10

Figure 3:
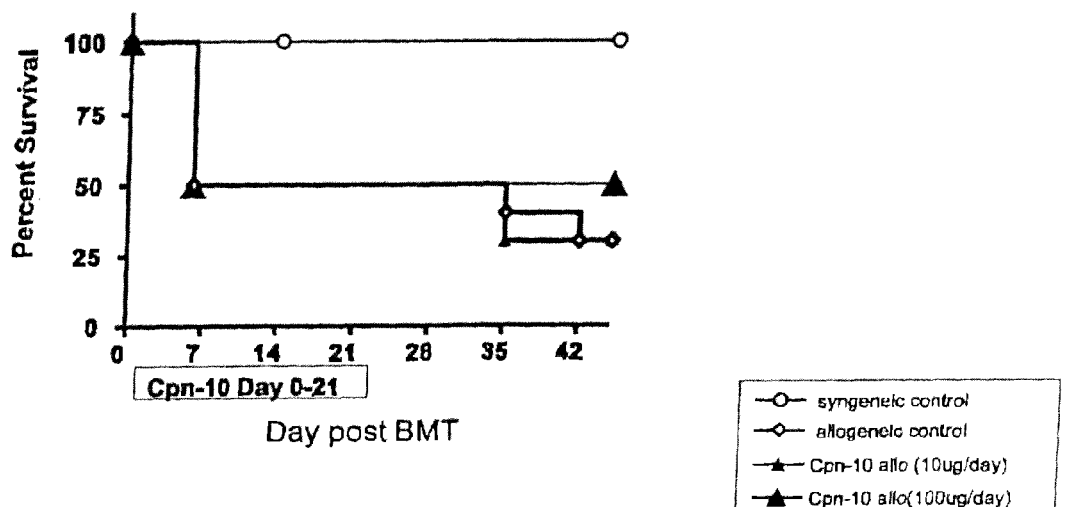
FIGS. 3A and B: Survival of mice after bone marrow transplantation and post-transplant treatment of cpn10. In the post transplant period (day 0 to 21) animals were injected subcutaneously with either vehicle (syngeneic, n=8 and allogeneic control group, n=10) or cpn10 (10 and 100 μg/animal/day: cpn10 10 μg/day allogeneic, n=10 and cpn10 100 μg/day allogeneic, n=10). B. Mice GVHD clinical scores plotted over time (0-45 days; **P<0.01).
Figure 3:
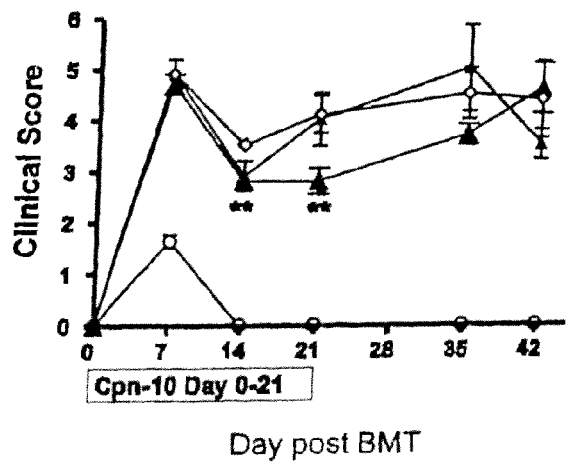

Bone marrow cells ($5 \times 10^6$/animal) and purified T cells (described above) from donor B6 mice were transplanted into lethally irradiated (1100 cGy) B6D2F1 recipient mice (allogeneic groups). B6D2F1 recipients in syngeneic control group received equal doses of B6D2F1 bone marrow and T cells. In the post-transplant period (day 0 to 21) animals were injected subcutaneously with either vehicle (syngeneic, n=8 and allogeneic control group, n=10) or cpn10 (10 and 100 μg/animal/day: cpn10 101.tg/day allogeneic, n=10 and cpn10 100 μg/day allogeneic, n=10). GVHD clinical scores (as described above) were determined as a measure of GVHD severity in surviving animals. Clinically milder GVHD was observed on day 14 and 21 in allogeneic animals injected with 100 μg/day of cpn10 compared to the vehicle treated allogeneic control (**P<0.01). There was no significant difference in the percent of survival between vehicle injected and cpn10 injected allogeneic groups. FIG. 3 shows mice survival curves by Kaplan-Meier analysis.

Administration of cpn10 after bone marrow transplantation (BMT) failed to prevent GVHD mortality and only briefly reduced morbidity as determined by GVHD clinical scores (FIG. 3B). Clinically milder GVHD was observed on day 14 and day 21 in allogeneic animals injected with 100 μg/day cpn10 compared to the vehicle-treated allogeneic control (**P<0.01).

Pre-Treatment Administration of cpn10

Recipient B6D2F1 and donor B6 mice were treated for 5 days pre-transplant with either cpn10 (100 μg/day/subcutaneously) or control diluent. Bone marrow ($5 \times 10^6$/animal) and T cells ($3 \times 10^6$/animal) harvested on day 6 from B6 donor mice were transplanted into lethally irradiated B6D2F1 recipients. Five groups of recipients were formed:

Group 1: Syngeneic control (n=8) represented B6D2F1 transplanted with syngeneic B6D2F1 bone marrow and T cells.

Group 2: Allogeneic control (n=10) consisted a diluent pre-treated B6D2F1 recipients transplanted with cells from diluent pre-treated B6 donors.

Group 3: Allogeneic recipient pre-treated (n=10), recipient B6D2F1 mice were treated pre-transplant with cpn10 and were transplanted with vehicle pre-treated B6 donor cells.

Group 4: Recipient B6D2F1 mice pretreated with diluent only that received transplant from cpn10 pre-treated B6 donors (allogeneic donor pretreated, n=10).

Group 5: Both B6D2F1 recipients and B6 donor mice were pretreated with cpn10 prior to transplantation (allogeneic recipient and donor pre-treated, n=10).

GVHD clinical scores as described above were determined as a measure of GVHD severity in surviving animals.

Figure 4:
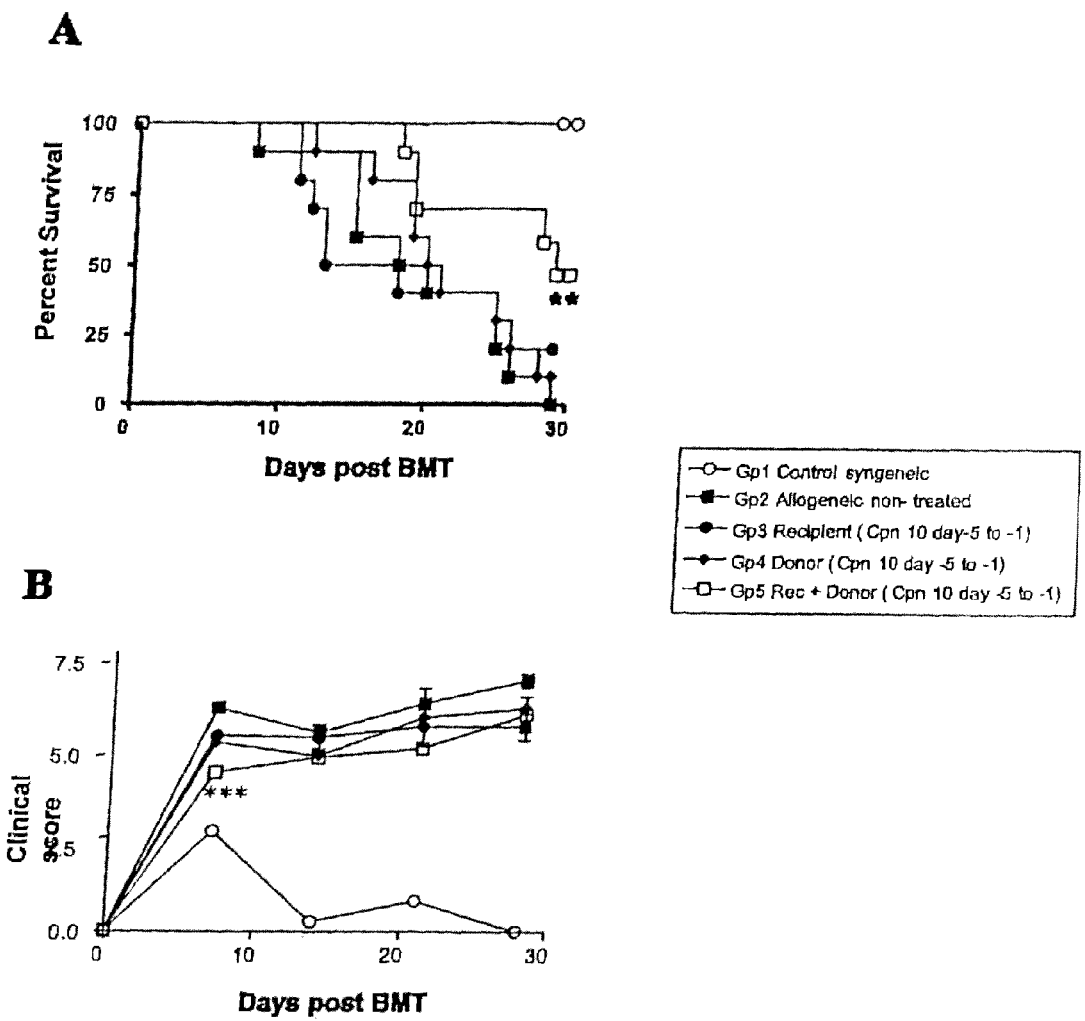
FIGS. 4A and B: Survival of mice after bone marrow transplantation and pre-transplant treatment of cpn10. Recipient and donor mice were treated for 5 days pre-transplant with subcutaneous injections of cpn10 (100 μg/day) or control diluent. Five groups of animals were then formed: Group 1: Syngeneic control (n=8) represented B6D2F1 transplanted with syngeneic B6D2F1 bone marrow and T cells; Group 2: Allogeneic control (n=10) consisted of diluent pre-treated B6D2F1 recipients transplanted with cells from diluent pre-treated B6 donors; Group 3: Allogeneic recipient pre-treated (n=10), recipient B6D2F1 mice were treated pre-transplant with cpn10 and were transplanted with vehicle pre-treated B6 donor cells; Group 4: Recipient B6D2F1 mice pretreated with diluent only that received transplant from cpn10 pre-treated B6 donors (allogeneic: donor pretreated, n=10); and Group 5: Both B6D2F1 recipients and B6 donor mice were pretreated with cpn10 prior to transplantation (allogeneic: recipient and donor pre-treated, n=10). (*P<0.01 versus allogeneic control) B. Mice GVHD clinical scores plotted over time (0-30 days; ***P<0.001).

Significantly lower clinical scores were observed on day 7 in Group 5 (both recipients and donors pretreated with cpn10 prior to transplantation) compared to the allogeneic control group (FIG. 4B; ***P<0.001). FIG. 4 shows mice survival curves by Kaplan-Meier analysis.

The administration of cpn10 to transplant donors and recipients for 5 days prior to transplant significantly delayed GVHD mortality (*P<0.01 versus allogeneic control). In addition, the severity of GVHD as determined by the clinical score was also reduced early after BMT. The ability of cpn10 to delay GVHD mortality when administered prior to BMT is consistent with the anti-inflammatory effect described here, i.e. a limitation of TNFα production (Hill et al., 1998 J. Clin. Invest., 102, 115-123; Hill et al., 1997, supra). The failure of cpn10 administration after BMT to prevent the development of GVHD, is consistent with an absence of an effect on T cell activation and differentiation at the doses and scheduling used in this Example, as was characterised in FIG. 3.

Transplant conditioning (lethal irradiation) in these models sets up a process of progressive GI tract injury, LPS leak and inflammatory cytokine generation which in turn induces further GI tract injury and so the process continues as a positive feedback loop. The process may be interrupted by pharmacological agents that protect the gut from radiation injury (such as IL-11 and Keratinocyte Growth Factor; Krijanovski et al., 1999, Blood, 94, 825-831), direct LPS antagonists (Cooke et al., 2001, J. Clin. Invest., 107, 1581-1589), or inhibitors of TNFα itself (Hill et al., 1997 supra). However, these agents tend to delay rather than prevent GVHD unless TNFα is neutralised completely, or there are additional effects on T cell activation and differentiation. Thus the delay in GVHD mortality by the administration of cpn10 is consistent with a limitation of LPS signaling and subsequent TNFα production early after BMT but also a failure to impact on subsequent alloreactive T cell function.

Therefore cpn10 has the potential to become an important therapeutic drug in the treatment of GVHD. The increased effectiveness of treatment of GVHD observed when both donor and recipient are administered with cpn10 prior to the transplant procedure is consistent with the fact that TNFα originates from both tissue or organ sources in the post transplant period (Cooke et al., 2000, J. Immunol., 165, 6612-6619; Speiser et al., 1997, J. Immunol., 158, 5185-5190).

Furthermore, cpn10 may be useful in the treatment of GVHD in combination with traditional immunosuppressive agents that limit the secondary adaptive immune response.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

The invention claimed is:

1. A method of treating graft versus host disease (GVHD), said method comprising
administering to a mammalian recipient a pharmaceutically-effective amount of chaperonin 10 (cpn10) comprising the amino acid sequence set forth in FIG. 1 (SEQ ID NO:1).

2. The method of claim 1 wherein the pharmaceutically-effective amount of cpn10 administered to the mammalian recipient is within the range 0.1-100 mg/kg body weight.

3. The method of claim 2 wherein the pharmaceutically-effective amount of cpn10 administered to the mammalian recipient is within the range 0.1-10 mg/kg body weight.

4. The method of claim 1 further comprising administering to said mammalian recipient at least one other immunosuppressive agent selected from the group consisting of cyclosporin, tacrolimus, sirolimus, mycophenolate mofetil and methotrexate.

5. The method of claim 1 further comprising administering a steroid to the mammalian recipient.

6. The method of claim 1 wherein the cpn10 is administered in a pharmaceutical composition.

* * * * *

SEQUENCE LISTING

```
<160> NUMBER OF SEQ ID NOS: 2

<210> SEQ ID NO 1
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ala Ala Gly Gln Ala Phe Arg Lys Phe Leu Pro Leu Phe Asp Arg Val
 1               5                  10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 2

His His His His His His
 1               5
```